United States Patent
Matsumoto et al.

[11] Patent Number: 5,597,921
[45] Date of Patent: Jan. 28, 1997

[54] INDOLO[2,3-B]QUINOXALINE DERIVATIVES

[75] Inventors: Taro Matsumoto; Hisaya Wada; Yoshihiro Migita; Katsuo Hatayama; Yoshinori Sekiguchi, all of Tokyo, Japan

[73] Assignee: Taisho Pharmaceutical Co., Ltd., Tokyo, Japan

[21] Appl. No.: 532,566

[22] PCT Filed: Apr. 22, 1994

[86] PCT No.: PCT/JP94/00673

§ 371 Date: Oct. 16, 1995

§ 102(e) Date: Oct. 16, 1995

[87] PCT Pub. No.: WO94/24135

PCT Pub. Date: Oct. 27, 1994

[30] Foreign Application Priority Data

Apr. 22, 1993 [JP] Japan .................... 5-095778

[51] Int. Cl.⁶ ............................ C07D 241/36
[52] U.S. Cl. ............................ 544/343
[58] Field of Search ............ 514/250; 544/343

[56] References Cited

U.S. PATENT DOCUMENTS

| | | | |
|---|---|---|---|
| 2,627,461 | 2/1953 | Friedman | 544/343 |
| 4,916,124 | 4/1990 | Bergman et al. | 414/211 |
| 4,990,510 | 2/1991 | Bergman et al. | 544/343 |

FOREIGN PATENT DOCUMENTS

| | | |
|---|---|---|
| 63-502588 | 9/1988 | Japan . |
| 63-502587 | 9/1988 | Japan . |
| 2-108058 | 4/1990 | Japan . |

*Primary Examiner*—Matthew V. Grumbling
*Attorney, Agent, or Firm*—Oblon, Spivak, McClelland, Maier & Neustadt, P.C.

[57] ABSTRACT

Indolo[2,3-b]quinoxaline derivatives represented by the following formula:

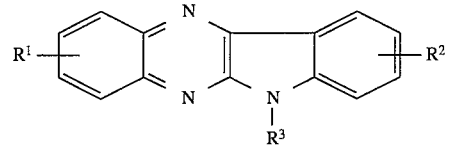

wherein one of $R^1$ and $R^2$ is a hydrogen atom and the other is a group of the formula:

$$-CH_2NHCCH_3(CH_2OH)_2,$$

etc, and $R^3$ is a hydrogen atom, a methyl group, etc.; and pharmaceutically acceptable salts thereof have an antitumor activity and are useful as medicines.

1 Claim, No Drawings

INDOLO[2,3-B]QUINOXALINE DERIVATIVES

This is a national stage application, filed under 37 C.F.R. 1.371 of PCT/JP94/00673, filed Apr. 22, 1994 and published as WO94/24135 Oct. 27, 1994.

TECHNICAL FIELD

The present invention relates to indolo[2,3-b]quinoxaline derivatives, and more particularly to novel indolo[2,3-b]quinoxaline derivatives and pharmaceutically acceptable salts having an antitumor activity.

BACKGROUND ART

Among known compounds having an indolo[2,3-b]quinoxaline ring with an antitumor activity are two kinds of the compounds reported in Japanese Patent Laid-open No. 63-502587 and ibid. 63-502588.

However, the antitumor effect of these compounds is insufficient.

Accordingly, an object of the present invention is to provide novel indolo[2,3-b]quinoxaline derivatives having an excellent antitumor activity.

DISCLOSURE OF THE INVENTION

An object of the present invention is to provide indolo[2,3-b]quinoxaline derivatives represented by Formula (I):

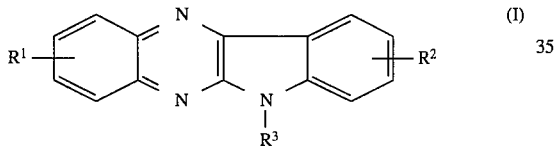

wherein
one of $R^1$ and $R^2$ is a hydrogen atom and the other is a group represented by Formula (II):

wherein $R^4$ is a hydrogen atom or a methyl group, $R^5$, $R^6$ and $R^7$ are the same or different, and are each a hydrogen atom, a straight or branched lower alkyl group or a group represented by Formula (III):

wherein X is a hydrogen atom, a straight or branched lower alkyl group or an acetyl group; and $R^3$ is a hydrogen atom, a methyl group or a group represented by Formula (IV):

wherein m is 1, 2 or 3, n is 1 or 2, P is an oxygen atom or a sulfur atom, and Q is a hydrogen atom, a hydroxyl group, a methoxy group, an ethoxy group, an acetoxy group or an acetamido group;
or pharmaceutically acceptable salts thereof.

BEST MODE FOR CARRYING OUT THE INVENTION

In the definitions of Formula (I), the straight or branched lower alkyl group for $R^5$, $R^6$, $R^7$ or X refers to a $C_1$–$C_6$ lower alkyl group such as, for example, a methyl group, an ethyl group, a propyl group, a butyl group, an isobutyl group, a pentyl group or a hexyl group.

The pharmaceutically acceptable salts of the indolo[2,3-b]quinoxaline derivative of Formula (I) refer to acid addition salts, which are those given by addition of a pharmacologically acceptable acid to the nitrogen atom in the molecule of the compound of Formula (I), and examples thereof are salts with mineral acids (e.g. hydrochloric acid, hydrobromic acid, hydroiodic acid, sulfuric acid, nitric acid or phosphoric acid), and salts with organic acids (e.g. acetic acid, oxalic acid, citric acid, tartaric acid, maleic acid, succinic acid, fumaric acid, p-toluenesulfonic acid, benzenesulfonic acid or methanesulfonic acid).

The indolo[2,3-b]quinoxaline derivatives of Formula (I) and the pharmaceutically acceptable salts thereof of the present invention can be prepared by reacting an intermediate of Formula (XII):

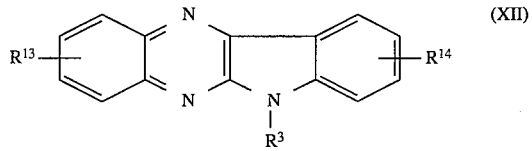

wherein one of $R^{13}$ and $R^{14}$ is a hydrogen atom and the other is a formyl group, a chloromethyl group or a bromomethyl group, and $R^3$ is as defined above, with an amine compound represented by Formula (XV):

wherein $R^4$ is a hydrogen atom or a methyl group, and $R^5$, $R^6$ and $R^7$ are the same or different and are each a hydrogen atom, a straight or branched lower alkyl group, or a group represented by Formula (III):

wherein X is a hydrogen atom, a straight or branched lower alkyl group or an acetyl group.

More specifically, the intermediate of Formula (XII) wherein one of $R^{13}$ and $R^{14}$ is a hydrogen atom and the other is a formyl group and the amine compound of Formula (XV) are heated to form an imino compound, which is then reduced with sodium borohydride or an alkoxy borohydride under heating to give a compound of Formula (I) as a salt-free form.

Furthermore, the intermediate of Formula (XII) wherein one of $R^{13}$ and $R^{14}$ is a hydrogen atom and the other is a chloromethyl group or a bromomethyl group is reacted with the amine compound of Formula (XV) under heating to give a compound of Formula (I) as a salt-free form.

An acid addition salt of the compound of Formula (I) can be obtained by treating the compound of Formula (I) with an acid such as hydrochloric acid. The acid addition salt is treated with an alkali compound to convert into a compound as a free form.

The intermediate of Formula (XII) can be prepared by the methods shown in the following Reaction Scheme 1, 2 or 3.

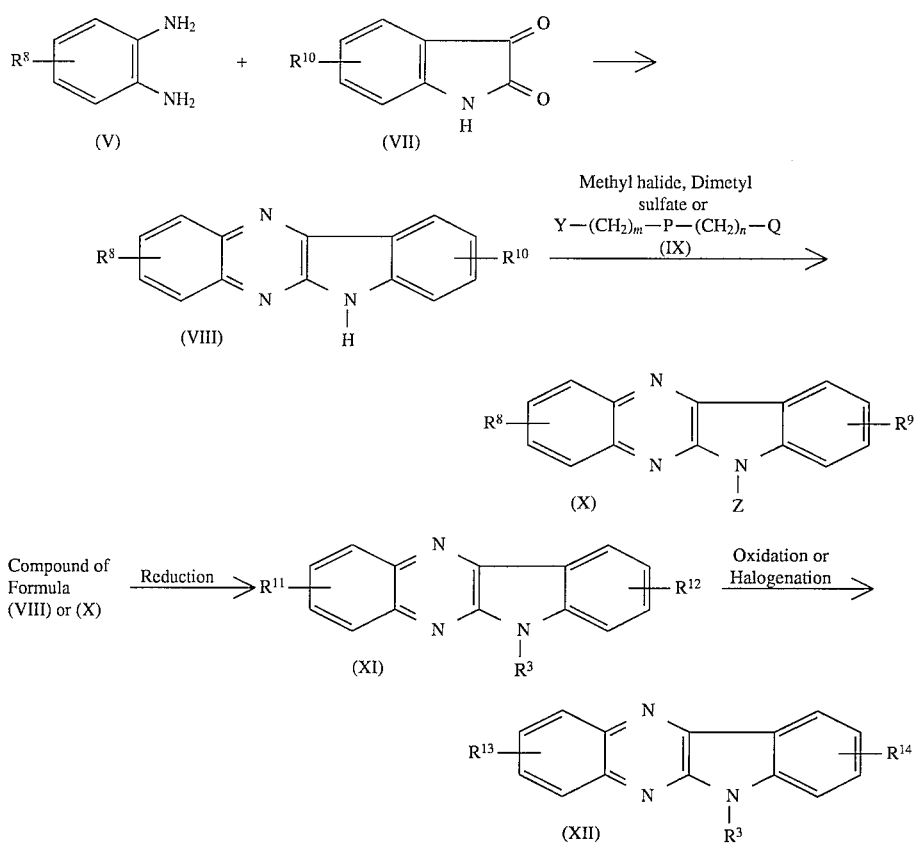

Reaction Scheme 1

In the 1,2-phenylenediamine compound of Formula (V), $R^8$ is a hydrogen atom or a group represented by Formula (VI):

$$-COOR^9 \qquad (VI)$$

wherein $R^9$ is a hydrogen atom or a lower alkyl group. The lower alkyl group for $R^9$ refers to a $C_1$–$C_6$ lower alkyl group, for example, such as a methyl group, an ethyl group, a propyl group, a butyl group, an isobutyl group, a pentyl group or a hexyl group. When $R^8$ in the compound of Formula (V) is a hydrogen atom, $R^{10}$ in the isatin compound of Formula (VII) is the group of Formula (VI), and when $R^8$ is the group of Formula (VI), $R^{10}$ is a hydrogen atom.

The 1,2-phenylenediamine compound of Formula (V) is condensed with the isatin compound of Formula (VII) in an organic acid such as acetic acid with heating to give a heterocycle compound of Formula (VIII). As clarified in the above definitions for the compound of Formula (VIII), one of $R^8$ and $R^{10}$ is a hydrogen atom and the other is the group of Formula (VI).

The heterocycle compound of Formula (VIII) is, if desired, reacted with a methyl halide (e.g. methyl iodide), dimethyl sulfate or a compound of Formula (IX) in the presence of sodium hydride in an aprotic polar solvent such as dimethyl sulfoxide to give a compound of Formula (X). In Formula (IX), m is 1, 2 or 3, n is 1 or 2, P is an oxygen atom or a sulfur atom, Q is a hydrogen atom, a hydroxyl group, a methoxy group, an ethoxy group, an acetoxy group or an acetamido group, and Y is a halogen atom, a mesyloxy group, a benzenesulfonyloxy group or a p-toluenesulfonyloxy group.

Subsequently, the heterocycle compound of Formula (VIII) or the compound of Formula (X) is reduced with lithium aluminum hydride or an alkoxy lithium aluminum hydride in an aprotic polar solvent such as tetrahydrofuran to convert the group of Formula (VI) defined for $R^8$ or $R^9$ in the compound of Formula (VIII) or (X) into a hydroxymethyl group, thereby giving a compound of Formula (XI). Reduction of the compound of Formula (VIII) gives a compound of Formula (XI) wherein $R^3$ is a hydrogen atom, and reduction of the compound of Formula (X) gives a compound of Formula (XI) wherein $R^3$ is a methyl group or a group of Formula (IV):

$$-(CH_2)_m-P-(CH_2)_n-Q- \qquad (IV)$$

wherein m, n, P and Q are as defined above.

The compound of Formula (XI) is oxidized with manganese dioxide in an organic solvent such as dioxane, tetrahydrofuran, carbon tetrachloride, chloroform or methylene chloride to convert the hydroxymethyl group defined for one of $R^{11}$ and $R^{12}$ in Formula (XI) into a formyl group, thereby giving an intermediate of Formula (XII).

Furthermore, the compound represented by Formula (XI) is halogenated with thionyl chloride or thionyl bromide in an organic solvent such as carbon tetrachloride, chloroform or methylene chloride to convert the hydroxymethyl group into a chloromethyl group or bromomethyl group, respectively, thereby giving an intermediate of Formula (XII).

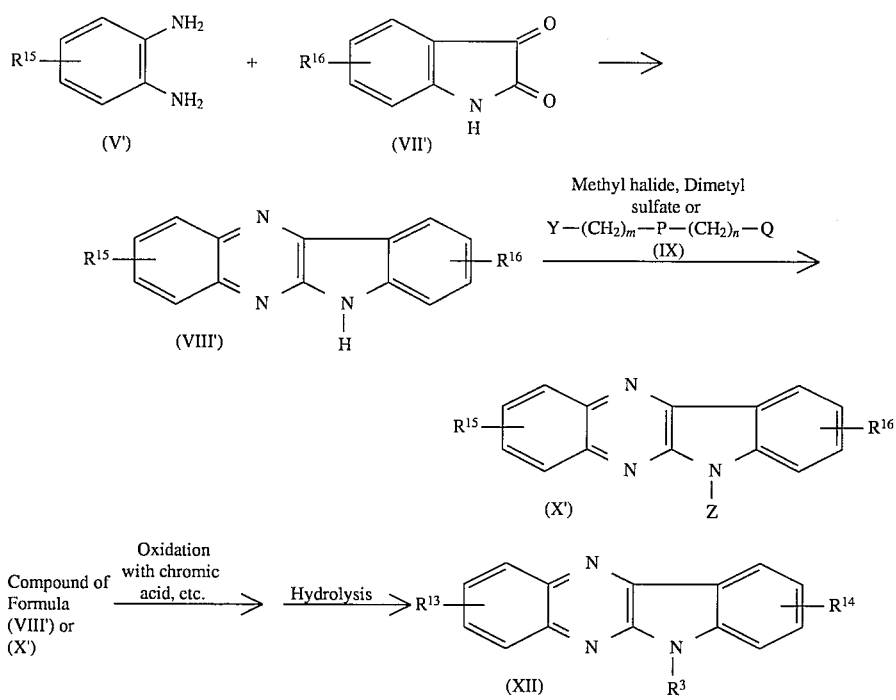

In the 1,2-phenylenediamine compound of Formula (V'), $R^{15}$ is a hydrogen atom or a methyl group.

When $R^{15}$ in Formula (V') is a hydrogen atom, $R^{16}$ in the isatin compound of Formula (VII') is a methyl group, and when $R^{15}$ is a methyl group, $R^{16}$ is a hydrogen atom.

The 1,2-phenylenediamine compound of Formula (V') is reacted with the isatin compound of Formula (VII') by a method similar to that shown in Reaction Scheme 1 to give a corresponding heterocycle compound of Formula (VIII'), which is then reacted by a method similar to that shown in Reaction Scheme 1 to give a compound of Formula (X').

The compound of Formula (VIII') or (X') wherein one of $R^{15}$ and $R^{16}$ is a hydrogen atom and the other is a methyl group is oxidized with, for example, chromic acid and then hydrolyzed to convert the methyl group for $R^{15}$ and $R^{16}$ into a formyl group, thereby giving an intermediate of Formula (XII).

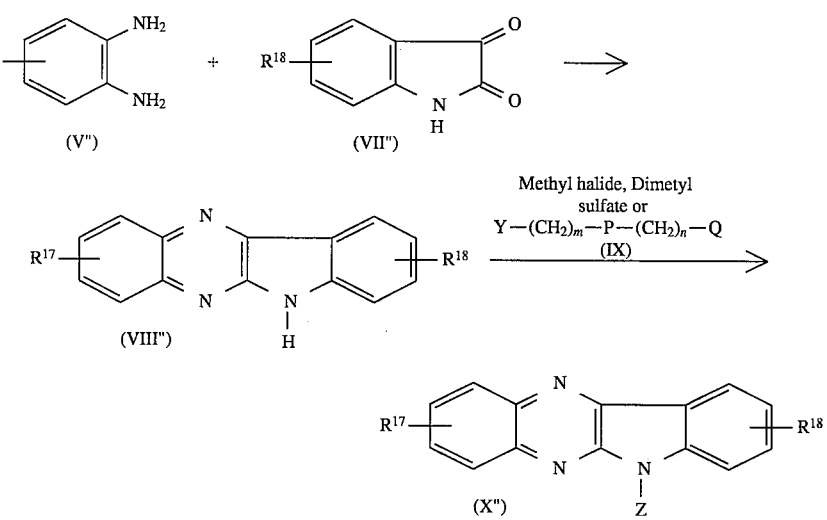

-continued
Reaction Scheme 3

Compound of Formula (VIII") or (X") →[Copper cyanide]

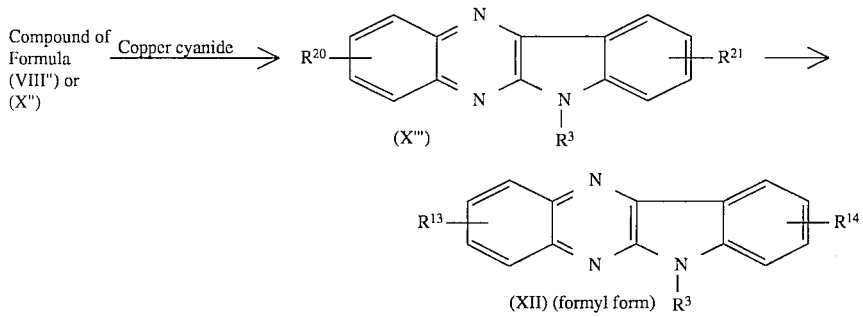

In the 1,2-phenylenediamine compound of Formula (V"), $R^{17}$ is a hydrogen atom or a halogen atom which is a chlorine atom or a bromine atom.

When $R^{17}$ in Formula (V") is a hydrogen atom, $R^{18}$ in the isatin compound of Formula (VII") is a chlorine atom or a bromine atom, and when $R^{17}$ is a chlorine atom or a bromine atom, $R^{18}$ is a hydrogen atom.

The 1,2-phenylenediamine compound of Formula (V") is reacted with the isatin compound of Formula (VII") by a method similar to that shown in Reaction Scheme 1 to give compounds of Formulae (VIII") and (X"), successively.

The compound of Formula (VIII") or (X") wherein one of $R^{17}$ and $R^{18}$ is a hydrogen atom and the other is a chlorine atom or a bromine atom is treated with copper cyanide to convert the halogen atom for $R^{17}$ or $R^{18}$ into a nitrile group, thereby giving a compound of Formula (X"'). In Formula (X"'), one of $R^{20}$ and $R^{21}$ is a hydrogen atom and the another is a nitrile group.

The compound of Formula (X"') wherein one of $R^{20}$ and $R^{21}$ is a hydrogen atom and the other is a nitrile group is reduced with lithium aluminum hydride, an alkoxy lithium aluminum hydride or an alkyl aluminum hydride in an organic solvent such as toluene, benzene or methylene chloride to give an intermediate (formyl form) of Formula (XII) wherein one of $R^{13}$ and $R^{14}$ is a hydrogen atom and the other is a formyl group.

An intermediate (halomethyl form) of Formula (XII) wherein one of $R^{13}$ and $R^{14}$ is a hydrogen atom and the other is a chloromethyl group or a bromomethyl group can be prepared by reducing the above intermediate (formyl form) of Formula (XII) with, for example, lithium aluminum hydride to give a compound of Formula (XI) shown in Reaction Scheme 1, followed by halogenation of the compound of Formula (XI) with thionyl chloride or thionyl bromide by a method similar to that shown in Reaction Scheme 1. In Reaction Scheme 3, the compound of Formula (IX) is as defined above, and Z defined for Formulae (X") and (X"') and $R^3$ defined for Formula (XII) are as defined above.

The indolo[2,3-b]quinoxaline derivatives of Formula (I) and pharmaceutically acceptable salts of the present invention have a potent antitumor activity, and therefore they are useful as medicines.

The indolo[2,3-b]quinoxaline derivatives of Formula (I) and pharmaceutically acceptable salts of the present invention can be administered orally or parenterally in a conventional dosage form. Examples of the form are tablets, powders, granules, dusts, capsules, solutions, emulsions, suspensions and injections, and all of which can be prepared by conventional practices. When used for humans, the dose may be different depending on the age, body weight, symptoms, route of administration and frequency of administration, but it is usually from 1 to 1000 mg per day.

The present invention is illustrated in more detail by the following Reference Examples, Examples and an Experiment.

EXAMPLE 1

Preparation of 2-methyl-2-(((6-methyl-indolo[2,3-b]quinoxalin-4-yl)-methyl)amino)1,3-propanediol Hydrochloride (1) Preparations of methyl 4-indolo[2,3-b]quinoxalinecarboxylate and methyl 1-indolo[2,3-b]quinoxalinecarboxylate A suspension of 20 g of methyl 2,3-diaminobenzoate and 17.7 g of isatin in 230 ml of acetic acid was heated under reflux for an hour. After completion of the reaction, the reaction solution was allowed to stand at room temperature overnight, and the resulting precipitate was collected by filtration. The precipitate was purified by silica gel column chromatography to give methyl 4-indolo[2,3-b]quinoxalinecarboxylate and methyl 1-indolo[2,3-b]quinoxalinecarboxylate.

Methyl 4-indolo[2,3-b]quinoxalinecarboxylate m.p. 278°–280° C. Yield 13.47 g

Methyl 1-indolo[2,3-b]quinoxalinecarboxylate m.p. 242°–244° C. Yield 2.08 g.

(2) Preparation of methyl 6-methyl-4-indolo[2,3-b]quinoxalinecarboxylate

To a solution of 4.30 g (15.5 mmol) of methyl 4-indolo [2,3-b]quinoxalinecarboxylate obtained in the above item (1) in dimethyl sulfoxide was added 0.81 g (18.6 mmol, 1.2 eq.) of sodium hydride, followed by stirring at room temperature. One hour later, 1.57 ml (18.6 mmol, 1.2 eq.) of methyl iodide was added, followed by stirring for a further 90 minutes. After addition of water to the mixture, the resulting precipitate was collected by filtration, and recrystallized from ethyl acetate—ether—n-hexane to give methyl 6-methyl-4-indolo[2,3-b]quinoxalinecarboxylate.

m.p. 155°–157° C. Yield 3.86 g.

(3) Preparation of 4-hydroxymethyl-6-methyl-indolo[2,3-b]quinoxaline

To a solution of 3.46 g (11.9 mmol) of methyl 6-methyl-4-indolo[2,3-b]quinoxalinecarboxylate obtained in the above item (2) in 120 ml of tetrahydrofuran was added 0.54 g (14.3 mmol, 1.2 mol eq.) of lithium aluminum hydride under ice-cooling, followed by stirring for an hour. 10 ml of ethyl acetate, 10 ml of water and 10 ml of 5% sodium hydroxide were added successively, and the resulting precipitate was collected by filtration. The precipitate was dissolved in a mixture of 1N hydrochloric acid and chloroform, and the organic layer was separated, combined with the filtrate, washed with an aqueous sodium chloride solution and dried over magnesium sulfate. After evaporation of the solvent, the residue was recrystallized from methylene chloride—methanol—n-hexane to give 4-hydroxymethyl-6-methylindolo[2,3-b]quinoxaline.

m.p. 201° C. Yield 2.88 g.

(4) Preparation of 6-methyl-4-indolo[2,3-b]quinoxalinealdehyde

To a solution of 2.36 g (9.0 mmol) of 4-hydroxymethyl-6-methylindolo[2,3-b]quinoxaline obtained in the above item (3) in 200 ml of methylene chloride was added 11.87 g (134 mmol, 15 eq.) of activated manganese dioxide, followed by stirring at room temperature for 8 hours. The excess manganese dioxide was filtered off through Celite, the filtrate was concentrated and purified by silica gel column chromatography (AcOEt: $CHCl_3$=1:9) to give 6-methyl-4-indolo[2,3-b]quinoxalinealdehyde.

m.p. 219°–221° C. Yield 1.84 g (5) Preparation of 2-methyl-2-(((6-methylindolo[2,3-b]quinoxalin-4-yl)methyl)amino)-1,3-propanediol A suspension of 0.26 g of 6-methyl-4-indolo[2,3-b]quinoxalinealdehyde obtained in the above item (4), 0.52 g of 2-amino-2-methyl-1,3-propanediolamine and 0.28 g of p-toluenesulfonic acid in toluene was heated under reflux. After evaporation of the solvent, 0.075 g of sodium borohydride and 30 ml of ethanol were added to the residue, followed by stirring at room temperature. After evaporation of the solvent, the residue was purified by silica gel column chromatography (MeOH: $CHCl_3$=1:9), followed by addition of 4N hydrogen chloride—ethyl acetate solution. The excess hydrogen chloride—ethyl acetate solution was evaporated under reduced pressure to give 2-methyl-2-(((6-methylindolo-[2,3-b]quinoxalin-4-yl)methyl)amino)-1,3-propanediol hydrochloride.

m.p. 278°–279° C. Yield 0.19 g.

EXAMPLE 2

Preparation of 2-methyl-2-(((6-methylindolo-[2,3-b]quinoxalin-1-yl)-methyl)amino)-1,3-propanediol Hydrochloride (1) Preparation of methyl 6-methyl-1-indolo[2,3-b]quinoxalinecarboxylate Methyl 1-indolo[2,3-b]quinoxalinecarboxylate obtained in Example 1(1) was treated by a method similar to that of Example 1(2) to give methyl 6-methyl-1-indolo[2,3-b]quinoxalinecarboxylate.

m.p. 194°–196° C.

(2) Preparation of 1-hydroxymethyl-6-methylindolo[2,3-b]quinoxaline

Methyl 6-methyl-1-indolo[2,3-b]quinoxalinecarboxylate was treated by a method similar to that of Example 1(3) to give 1-hydroxymethyl-6-methylindolo[2,3-b]quinoxaline.

m.p. 191°–194° C.

(3) Preparation of 6-methyl-1-indolo[2,3-b]quinoxalinealdehyde

1-Hydroxymethyl-6-methylindolo[2,3-b]quinoxaline was treated by a method similar to that of Example 1(4) to give 6-methyl-1-indolo[2,3-b]quinoxalinealdehyde.

m.p. 257.5°–258° C.

(4) Preparation of 2-methyl-2-(((6-methylindolo[2,3-b]quinoxalin-1-yl)methyl)amino)-1,3-propanediol 6-Methyl-1-indolo[2,3-b]quinoxalinealdehyde was treated by a method similar to that of Example 1(5) to give 2-methyl-2-(((6-methylindolo[2,3-b]quinoxalin-1-yl)methyl)amino)-1,3-propanediol hydrochloride.

m.p. 263°–265° C. (decomposition).

EXAMPLE 3

Preparation of 2-methyl-2-(((6-methylindolo[2,3-b]quinoxalin-7-yl)-methyl)amino)-1,3-propanediol Hydrochloride (1) Preparation of methyl 7-indolo[2,3-b]quinoxalinecarboxylate A suspension of 3.96 g of 1,2-phenylenediamine and 7.00 g of 7-isatincarboxylic acid in 70 ml of acetic acid was heated under reflux for an hour. After completion of the reaction, the reaction solution was allowed to cool to room temperature, followed by addition of water, and resulting precipitate was collected by filtration. The thus obtained 7-indolo[2,3-b]quinolinecarboxylic acid and 170 ml of thionyl chloride were refluxed for 2 hours, and the excess thionyl chloride was evaporated. The residue, after addition of 250 ml of methanol, was stirred overnight. After addition of water, the resulting precipitate was collected by filtration, and purified by silica gel column chromatography to give methyl 7-indolo[2,3-b]quinoxalinecarboxylate.

m.p. 251°–255° C. Yield 4.04 g.

(2) Preparation of methyl 6-methyl-7-indolo[2,3-b]quinoxalinecarboxylate

Methyl 7-indolo[2,3-b]quinoxalinecarboxylate was treated by a method similar to that of Example 1(2) to give methyl 6-methyl-7-indolo[2,3-b]quinoxalinecarboxylate.

m.p. 184°–186° C.

(3) Preparation of 7-hydroxymethyl-6-methylindolo[2,3-b]quinoxaline

Methyl 6-methyl-7-indolo[2,3-b]quinoxalinecarboxylate was treated by a method similar to that of Example 1(3) to give 7-hydroxymethyl-6-methylindolo[2,3-b]quinoxaline.

m.p. 237°–238° C.

(4) Preparation of 6-methyl-7-indolo[2,3-b]quinoxalinealdehyde

7-Hydroxymethyl-6-methylindolo[2,3-b]quinoxaline was treated by a method similar to that of Example 1(4) to give 6-methyl-7-indolo[2,3-b]quinoxalinealdehyde.

m.p. 220° C.

(5) Preparation of 2-methyl-2-(((6-methylindolo[2,3-b]quinoxalin-7-yl)methyl)amino)-1,3-propanediol 6-Methyl-7-indolo[2,3-b]quinoxalinealdehyde was treated by a method similar to that of Example 1(5) to give 2-methyl-2-(((6-methylindolo[2,3-b]quinoxalin-7-yl)methyl)amino)-1,3-propanediol hydrochloride.

m.p. 284°–286° C.

EXAMPLE 4

Preparation of 2-methyl-2-(((6-methylindolo[2,3-b]quinoxalin-9-yl)-methyl)amino)-1,3-propanediol Hydrochloride (1) Preparation of 9-methylindolo[2,3,b]quinoxaline A suspension of 4.33 g of 1,2-phenylenediamine and 6.45 g of 5-methylisatin in 500 ml of acetic acid was refluxed for 2 hours. To the reaction solution was added 50 ml of water, and the precipitate was collected by filtration, dried and recrystallized from chloroform—ethanol—tetrahydrofuran to give 9-methylindolo-[2,3,-b]quinoxaline.

m.p. 299°–300° C. Yield 4.20 g.

(2) Preparation of 6,9-dimethylindolo[2,3-b]quinoxaline

9-Methylindolo[2,3-b]quinoxaline was treated by a method similar to that of Example 1(2) to give 6,9-dimethylindolo[2,3-b]quinoxaline.

m.p. 163°–164° C.

(3) Preparation of 9-diacetoxymethyl-6-methylindolo[2,3-b]quinoxaline

To a solution of 5.50 g of 6,9-dimethylindolo[2,3-b]quinoxaline in 25 ml of acetic anhydride was added 4.5 ml of conc. sulfuric acid under ice-cooling, followed by adding dropwise a solution of 6.24 g of chromic anhydride in 28 ml of acetic anhydride at 10° C. or below, and the mixture was stirred for 40 minutes. The reaction solution was poured into 300 ml of ice water, and extracted twice with 200 ml of chloroform. The combined organic layer was washed with an aqueous sodium chloride solution and dried over anhydrous sodium sulfate. After evaporation of the solvent under reduced pressure, the residue was treated by silica gel column chromatography (chloroform), and the resulting fractions were recrystallized from chloroform—ethanol to give 1.32 g of 9-diacetoxy-methyl-6-methylindolo[2,3-b]quinoxaline.

m.p. 220°–224° C.

(4) Preparation of 6-methyl-9-indolo[2,3-b]quinoxalinealdehyde

To a suspension of 1.29 g of 9-diacetoxy-methyl-6-methylindolo[2,3-b]-quinoxaline in 50 ml of tetrahydrofuran were added 1 ml of water and 1 ml of conc. sulfuric acid, followed by reflux for 5 hours. The reaction solution was allowed to stand overnight, and the resulting crystals were collected by filtration to give 0.78 g of 6-methyl-9-indolo[2,3-b]quinoxalinealdehyde.

m.p. 228°–230° C.

(5) Preparation of 2-methyl-2-(((6-methylindolo[2,3-b]quinoxalin-9-yl)methyl)amino)-1,3-propanediol 6-Methyl-9-indolo[2,3-b]quinoxalinealdehyde was treated by a method similar to that of Example 1(5) to give 2-methyl-2-(((6-methylindolo[2,3-b]quinoxalin-9-yl)methyl)amino)-1,3-propanediol hydrochloride.

m.p. 200°–202° C.

EXAMPLE 5

Preparation of 2-(((6-methylindolo[2,3-b]quinoxalin-4-yl)methyl)amino)-1,3-propanediol Hydrochloride (1) Preparation of 4-chloromethyl-6-methylindolo[2,3-b]quinoxaline To a solution of 304 mg (1.16 mmol) of 4-hydroxymethyl-6-methylindolo[2,3-b]quinoxaline in 30 ml of methylene chloride was added 0.126 ml (1.73 mmol, 1.5 eq.) of thionyl chloride under ice-cooling, followed by stirring for 3 hours. The reaction solution was poured into 50 ml of ice water, and extracted with methylene chloride. The organic layer was washed 3 times with a saturated aqueous sodium hydrogen carbonate solution and dried over anhydrous sodium sulfate. Evaporation of the solvent gave 335 mg of the crude product 4-chloromethyl-6-methylindolo[2,3-b]quinoxaline, which was used for the next reaction without further purification.

m.p. 204°–206° C.

(2) Preparation of 2-(((6-methylindolo[2,3-b]quinoxalin-4-yl)methyl)amino)-1,3-propanediol A mixture of 286 mg of the crude product 4-chloromethyl-6-methylindolo[2,3-b]quinoxaline obtained in the above item (1) and 4,629 g (50.8 mmol) of 2-amino-1,3-propanediol was heated at 150° C. for 10% minutes. To the cooled reaction solution were added 10 methanol—methylene chloride and water, and the organic layer was separated. The aqueous layer was further extracted 4 times with 10% methanol—methylene chloride, and the combined organic layer was dried over anhydrous sodium sulfate and evaporated under reduced pressure. The residue was purified by silica gel column chromatography (MeOH: $CHCl_3$=1:10). To the fractions was added 4N hydrogen chloride—ethyl acetate solution, and the excess hydrogen chloride—ethyl acetate solution was evaporated under reduced pressure to give the hydrochloride, which was then recrystallized from ethanol to give 2-(((6-methylindolo[2,3-b]quinoxalin-4-yl)methyl)amino)-1,3-propanediol hydrochloride.

m.p. 247°–249° C. Yield 239 mg.

EXAMPLE 6

Preparation of a mixture of 2-methyl-2-(((6-methylindolo[2,3-b]quinoxalin-2-yl)methyl)amino)-1,3-propanediol hydrochloride and 2-methyl-2-(((6-methylindolo[2,3-b]quinoxalin-3-yl)methyl)amino)-1,3-propanediol Hydrochloride (1) Preparation of a mixture of 2-cyano-6-methylindolo[2,3-b]quinoxaline and 3-cyano-6-methylindolo[2,3-b]quinoxaline A solution of 2.66 g (20 mmol) of 3,4-diaminobenzonitrile and 3.22 g (1.0 eq.) of 1-methylisatin in 25 ml of acetic acid was refluxed for 2 hours. The reaction solution was allowed to stand at room temperature, and the resulting crystals were collected by filtration and recrystallized from chloroform—ethanol to give a mixture of 2-cyano-6-methylindolo[2,3-b]quinoxaline and 3-cyano-6-methylindolo[2,3-b]quinoxaline.

m.p. 237°–246° C. Yield 4.03 g.

(2) Preparation of 6-methyl-2-indolo[2,3-b]quinoxalinealdehyde and 6-methyl-3-indolo[2,3-b]quinoxalinealdehyde To a solution of 1.70 g (6.58 mmol) of the mixture obtained in the above item (1) in 300 ml of toluene was added a solution of 7.6 ml of diisobutyl aluminum hydride in 1.02 mol/l of toluene under a nitrogen stream at room temperature, and the stirring was continued for 2 hours. 2 ml of ethyl acetate was added to the reaction solution, followed by stirring for a further one hour to complete the reaction. After addition of water and dilute hydrochloric acid to the reaction solution, the mixture was extracted twice with chloroform, and the combined extract was washed with an aqueous sodium chloride solution and dried over sodium sulfate. The solvent was evaporated, and the residue was subjected to silica gel column chromatography (MeOH: $CHCl_3$=0.1:10), and the resulting fractions were recrystallized from chloroform—ethanol to give a mixture of 6-methyl-2-indolo[2,3-b]quinoxalinealdehyde and 6-methyl-3-indolo[2,3-b]quinoxalinealdehyde.

m.p. 214°–219° C. Yield 1.02 g.

(3) Synthesis of a mixture of 2-methyl-2-(((6-methylindolo[2,3-b]quinoxalin-2-yl)methyl)amino)-1,3-propanediol and 2-methyl-2-(((6-methylindolo[2,3-b]quinoxalin-3-yl)methyl)amino)-1,3-propanediol The mixture obtained in the above item (2) was treated by a method similar to that of Example 1(5) to give a mixture of 2-methyl-2-(((6-methylindolo[2,3-b]quinoxalin-2-yl)methyl)amino)-1,3-propanediol hydrochloride and 2-methyl-2-(((6-methylindolo[2,3-b]quinoxalin-3-yl)methyl)amino)-1,3-propanediol hydrochloride.

m.p. 243°–248° C. (decomposition).

EXAMPLE 7

Preparation of
2-methyl-2-(((6-methylindolo[2,3-b]quinoxalin-8-yl)-
methyl)amino)-1,3-propanediol Hydrochloride (1) Preparation of 8-bromoindolo[2,3-b]quinoxaline A solution of 15.18 g (67.2 mmol) of 6-bromoisatin and 7.26 g (1.0 eq.) of 1,2-phenylenediamine in 250 ml of butyric acid was refluxed for 4 hours, followed by allowing to stand at room temperature for 16 hours. The precipitate was collected by filtration to give 8-bromoindolo[2,3-b]quinoxaline.

m.p. >300° C. Yield 17.60 g.

(2) Preparation of 8-bromo-6-methylindolo[2,3-b]quinoxaline

8-Bromoindolo[2,3-b]quinoxaline obtained in the above item (1) was treated by a method similar to that of Example 1 to give 8-bromo-6-methylindolo[2,3-b]quinoxaline.

m.p. 182°–183° C.

(3) Preparation of 8-cyano-6-methylindolo[2,3-b]quinoxaline

To 8.00 g (25.6 mmol) of 8-bromo-6-methylindolo[2,3-b]quinoxaline obtained in the above item (2) were added 8.00 g of copper cyanide, 35 ml of dimethyl sulfoxide and 3.8 ml of pyridine, followed by reflux for an hour. The reaction solution, while hot, was poured into ice water—chloroform with stirring, and extracted with chloroform. The extract was evaporated to dryness under reduced pressure, the residue was subjected to silica gel column chromatography (chloroform), and the resulting fractions were recrystallized from chloroform—ethanol to give 8-cyano-6-methylindolo[2,3-b]quinoxaline.

m.p. 284°–287° C. Yield 1.96 g.

(4) Preparation of 6-methyl-8-indolo[2,3-b]quinoxalinealdehyde

8-Cyano-6-methylindolo[2,3-b]quinoxaline obtained in the above item (3) was treated by a method similar to that of Example 6(4) to give 6-methyl-8-indolo[2,3- b]quinoxalinealdehyde.

m.p. 237°–238° C.

(5) Preparation of 2-methyl-2-(((6-methylindolo[2,3-b]quinoxalin-8-yl)methyl)amino)-1,3-propanediol 6-Methyl-8-indolo[2,3-b]quinoxalinealdehyde obtained in the above item (4) was treated by a method similar to that of Example 1 (5) to give 2-methyl-2-(((6-methylindolo[2,3-b]quinoxalin-8-yl)methyl)amino)-1,3-propanediol hydrochloride.

m.p. 273°–275° C. (decomposition).

EXAMPLE 8

Preparation of
2-methyl-2-(((6-methylindolo[2,3-b]quinoxalin-10-yl)-
methyl)amino)-1,3-propanediol Hydrochloride (1) Preparation of 10-bromoindolo[2,3-b]quinoxaline A solution of 3.40 g (15.0 mmol) of 4-bromoisatin and 1.63 g (1 eq.) of 1,2-phenylenediamine in 50 ml of acetic acid was refluxed for 2 hours. The reaction solution was allowed to stand at room temperature for 16 hours, and the resulting precipitate was collected by filtration to give 10-bromoindolo[2,3-b]quinoxaline.

m.p. >300° C. Yield 1.82 g.

(2) Preparation of 10-bromo-6-methylindolo[2,3-b]quinoxaline

10-Bromoindolo[2,3-b]quinoxaline obtained in the above item (1) was treated by a method similar to that of Example 1(2) to give 10-bromo-6-methylindolo[2,3-b]quinoxaline.

m.p. 208°–209° C.

(3) Preparation of 10-cyano-6-methylindolo[2,3-b]quinoxaline

To 15.14 g of 10-bromo-6-methylindolo[2,3-b]quinoxaline obtained in the above item (2) were added 8.02 g of copper cyanide, 67 ml of dimethyl sulfoxide and 7.1 ml of pyridine, followed by heating at 180° C. with stirring for 40 minutes. Then, the mixture was worked up by a method similar to that of Example 7(3) to give 10-cyano-6-methylindolo[2,3-b]quinoxaline.

m.p. 237°–239°0 C. Yield 10.03 g.

(4) Preparation of 6-methyl-10-indolo[2,3-b]quinoxalinealdehyde

10-Cyano-6-methylindolo[2,3-b]quinoxaline obtained in the above item (3) was treated by a method similar to that of Example 6(2) to give 6-methylindolo[2,3-b]quinoxalinealdehyde.

m.p. 219°–220° C.

(5) Preparation of 2-methyl-2-(((6-methylindolo[2,3-b]quinoxalin-10-yl)methyl)amino)-1,3-propanediol 6-Methyl-10-indolo[2,3-b]quinoxalinealdehyde obtained in the above item (4) was treated by a method similar to that of Example 1(5) to give 2-methyl-2-(((6-methylindolo[2,3-b]quinoxalin-10-yl)methyl)amino)-1,3-propanediol hydrochloride.

m.p. 250°–252° C. (decomposition).

Experiment

P388 Lymphocytic Leukemia Test (1) Test animal

Female, CDF1 mice were intraperitoneally transplanted with each of $1\times10^6$ cells of P388 lymphocytic leukemia passaged on female, DBA/2 mice. The transplantation day refers to day 0.

(2) Administration route

A suspension of the test drug in 0.5% of gum arabic/saline solution was administered intraperitoneally once a day, 5 times in all, from day 1 to day 5. A solution of 5-fluorouracil in saline served as a comparative drug, and similarly administered. Control group were similarly administered with only 0.5% gum arabic/saline solution. Eight animals were used for the treated group with the test drugs and the comparative drug, respectively, and 16 animals for control group.

(3) Evaluation method

Effect evaluation was carried out according to the criterion [Venditti JM, Wesley RA, Plowman J, Adv. Pharmacol. Chemother., 20: 1p (1989)] of the National Cancer Institute of the United States (NCI).

The survivors of each group were recorded for 30 days, and the value of T/C×100 (%) was calculated from the median survival times for the treated animals (T) and the control animals(C).

When the T/C value is 125 or more, the drug is judged to be effective.

(4) Test results

The test results are shown in Table 1.

The compounds of the present invention indicated great value of T/C×100.

TABLE 1

| Test drug | Effect against P388 in mouse | |
|---|---|---|
| | dose (mg/kg) | T/C × 100 |
| Compound obtained in Example 1 | 100 | 58 |
| | 25 | >306 |
| | 6.25 | 142 |
| Compound obtained in Example 2 | 25 | 169 |
| | 6.25 | 149 |
| Compound obtained in Example 3 | 100 | 127 |
| | 25 | 113 |
| | 6.25 | 101 |
| 5-fluorouracil | 100 | — |
| | 25 | 176 |
| | 6.25 | 167 |

Industrial Applicability

The indolo[2,3-b]quinoxaline derivatives and pharmaceutically acceptable salts of the present invention have a potent antitumor activity, and therefore they are useful as antitumor agents.

We claim:

1. An indolo[2,3-b]quinoxaline derivative represented by Formula (I):

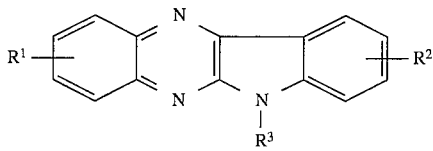 (I)

wherein one of $R^1$ and $R^2$ is a hydrogen atom and the other is a group represented by Formula (II):

 (II)

wherein $R^4$ is a hydrogen atom or a methyl group, $R^5$, $R^6$ and $R^7$ are the same or different, and are each a hydrogen atom, a straight or branched lower alkyl group or a group represented by Formula (III):

 (III)

wherein X is a hydrogen atom, a straight or branched lower alkyl group or an acetyl group; and $R_3$ is a hydrogen atom, a methyl group or a group represented by Formula (IV):

 (IV)

wherein m is 1, 2 or 3, n is 1 or 2, P is an oxygen atom or a sulfur atom, and Q is a hydrogen atom, a hydroxyl group, a methoxy group, an ethoxy group, an acetoxy group or an acetamido group;

or a pharmaceutically acceptable salt thereof.

* * * * *